United States Patent [19]

Papahadjopoulos et al.

[11] Patent Number: 4,806,466

[45] Date of Patent: Feb. 21, 1989

[54] CELL AGGLUTINATION REAGENT COMPRISING CONJUGATES OF ANTIBODY COVALENTLY BOUND TO LIPOSOMES

[75] Inventors: Demetrios P. Papahadjopoulos, Lafayette; Timothy D. Heath, San Francisco, both of Calif.

[73] Assignee: The Regents of the University of California, Berkeley, Calif.

[21] Appl. No.: 840,054

[22] Filed: Mar. 17, 1986

Related U.S. Application Data

[60] Division of Ser. No. 316,126, Oct. 29, 1981, Pat. No. 4,598,051, which is a continuation-in-part of Ser. No. 129,654, Mar. 12, 1980, abandoned.

[51] Int. Cl.$^4$ ................. G01N 33/554; G01N 33/555; G01N 33/563; G01N 33/577
[52] U.S. Cl. ......................... 435/7; 264/4.1; 264/4.3; 424/11; 436/512; 436/519; 436/520; 436/548; 436/829
[58] Field of Search ............... 436/512, 519, 520, 533, 436/534, 829; 424/11; 264/4.1, 4.3; 435/7

[56] References Cited

U.S. PATENT DOCUMENTS

| | | |
|---|---|---|
| 3,850,578 | 11/1974 | McConnell . |
| 3,887,698 | 6/1975 | McConnell et al. . |
| 4,193,983 | 3/1980 | Ullman et al. . |
| 4,195,074 | 3/1980 | Safford . |
| 4,232,001 | 11/1980 | Jensen . |
| 4,396,630 | 8/1983 | Riedl et al. . |
| 4,429,008 | 1/1984 | Martin .............................. 436/829 X |
| 4,483,928 | 11/1984 | Suzuta .............................. 436/829 X |
| 4,636,479 | 1/1987 | Martin .............................. 436/829 X |
| 4,737,323 | 4/1988 | Martin .............................. 436/829 X |
| 4,752,425 | 6/1988 | Martin .............................. 436/829 X |
| 4,762,915 | 8/1988 | Kung .............................. 264/4.1 X |

FOREIGN PATENT DOCUMENTS

| | | |
|---|---|---|
| 497036 | 11/1978 | Australia . |
| 0038181 | 10/1981 | European Pat. Off. . |
| 0040058 | 11/1981 | European Pat. Off. . |
| 2650502 | 5/1978 | Fed. Rep. of Germany . |
| 2051360 | 1/1981 | United Kingdom . |
| 2105463 | 3/1983 | United Kingdom . |

OTHER PUBLICATIONS

Martin, F. J. et al., *J. Cell Biol.* (1976), 70(3), 494–505.
Chemical Abstracts, 85:91227y (1976).
Martin, *Biochemistry*, 20 (Jul. 1981), pp. 4229–4238.
Torchilin et al., *Biochimica et Biophysica Acta*, 602 (1980), pp. 511–521.
Torchilin et al., *Biochemical and Biophysical Research Communications*, 89, No. 4, (1979), pp. 1114–1119.
Huang et al., *Journal of Biological Chemistry*, 255, No. 17, (1980), pp. 8015–8018.
Torchilin et al., *FEBS Letters*, 111, No. 1 (1980), pp. 184–188.
Lesserman et al., *Nature*, 288 (Dec. 11, 1980), pp. 602–604.
Heath et al., *Science*, 210 (Oct. 31, 1980), pp. 539–541.
Heath et al., *Biochimica et Biophysica Acta*, 640 (1981), pp. 66–81.
Torchilin et al., *Biochemical and Biophysical Research Communications*, vol. 85, No. 3, pp. 983–990 (1978).
Sinha et al., *FEBS Proc. Abstracts*, (May 1, 1980), vol. 39, No. 6, Ab. No. 825.
Sinha et al., *Biochemical and Biophysical Research Communications*, vol. 90, No. 2, (1979), pp. 554–560.
Fry et al., *Jour. Immunological Methods*, 11 (1976), pp. 185–193.
Chemical Abstracts, 95:59698y (1981).
Chem. Abstracts, 90:68851s, (1979).
Chem. Abstracts, 81:150043c, (1974).
"Ultrogel and Magnogel," *Prac. Guide for Use in Affinity Chromatography*, (1979), Pharmindustrie, Clinchy, France.
Sanderson et al., *Immunology* 20(6), pp. 1061–1065 (1971).
Urdal et al., *Journal of Biol. Chem.* 225 (21), pp. 10509–10516 (1980).
Sinha, *Fed. Proc.*, vol. 38, No. 3, Mar. 1, 1979, p. 942, Abs. No. 3766.
Rector et al., *Journal of Immunological Methods*, 24 (1978), pp. 321–336.
Carlsson, *Biochem. J.* (1978) 173, pp. 723–737.

Primary Examiner—Sidney Marantz
Attorney, Agent, or Firm—Majestic, Parsons, Siebert & Hsue

[57] ABSTRACT

A number of naturally occurring antibodies to human erythrocyte surface antigens are capable of combining with their specific antigens (for example, Rhesus factor), but are not capable of producing visible hemagglutination. Also, the sensitivity of many diagnostic methods, such as in human blood typing, depends upon cell agglutination.

The present invention provides liposome-protein conjugates, especially useful for hemagglutination assays, having an enhanced agglutination capacity with respect to antibody from which the conjugates are derived.

14 Claims, No Drawings

CELL AGGLUTINATION REAGENT COMPRISING CONJUGATES OF ANTIBODY COVALENTLY BOUND TO LIPOSOMES

The invention described herein was made in the course of work under a grant or award from the Department of Health and Human Services.

This is a divisional of application Ser. No. 316,125, filed Oct. 29, 1981, now U.S. Pat. No. 4,598,051 which was a continuation-in-part of application U.S. Ser. No. 129,654, filed Mar. 12, 1980, now abandoned.

FIELD OF THE INVENTION

The present invention relates generally to liposome conjugates, and more particularly to liposome-protein conjugates which have an enhanced agglutination ability, can rapidly and sensitively agglutinate cells such as erythrocytes, lymphocytes, and leukocytes, and which are useful in applications such as blood typing.

BACKGROUND OF THE INVENTION

Liposomes are now well recognized as useful for delivery of therapeutic agents, such as cytotoxic drugs or other macromolecules capable of modifying cell behaviour, to in vivo sites. For example, U.S. Pat. No. 3,993,754, inventors Rahman, et al, issued Nov. 23, 1976, discloses an improved method for chemotherapy of malignant tumors in which an antitumor drug is encapsulated within liposomes and the liposomes containing the encapsulated drug are injected into an animal or man.

It has been suggested that target, or in vivo site, specificity might be conferred on liposomes by their association with specific antibodies or lectins. Methods of associating antibodies with liposomes have been described, and may be generally divided into two groups—nonspecific association and covalent attachment.

Nonspecific association appears to rely upon the affinity of the Fc portion of the antibody for the hydrophobic region of the lipid bilayer. However, nonspecific association appears incapable of associating more than about 15-30 microgram per micromole of lipid. Also, nonspecific association has little practical value because the liposomes are rendered more permeable than their encapsulated contents and protein aggregation is produced during formation of the nonspecifically associated liposome-protein.

Prior to preparation of the covalently attached protein of coupled-protein species described in U.S. patent application Ser. No. 129,654, attempts to covalently attach protein to liposomes had been unsatisfactory. For example, some of the prior attempts had involved modifications of the proteins which tended to denature the protein, and thus a substantial loss of biological activity had ensued. Other attempts to covalently attach protein to liposomes had produced very small amounts of specific attachment.

By contrast, activated liposomes in accordance with U.S. patent application Ser. No. 129,654 are readily and efficiently covalently bound to a variety of biologically active proteins with at least about 40 microgram of protein per micromole of lipid. For example, use of the activated liposomes has achieved coupling of up to about 200 microgram of F(ab')$_2$ per micromole of lipid; further, such coupled liposome-protein species were shown to have an improved hemagglutinating titre by comparison to the original, soluble antibody from which they were derived.

Very recently, another efficient method for coupling protein to liposomes has reported coupling of up to 600 microgram of Fab' per micromole of phospholipid via a disulfide interchange reaction. Martin, et al., *Biochemistry*, 20, pages 4429-4238 (July, 1981).

Meanwhile, agglutination methods are known and useful for applications such as blood typing. However, many such methods have had to be performed indirectly, or have been of relatively low sensitivity. For example, the Coombs test is an indirect agglutination method in the sense that a secondary, or intermediate, antibody must be used. Further, detection of antibodies which do not produce positive agglutination (e.g. visible agglutination) when combined with their specific antigens has presented difficulties in applications such as blood crossmatching. Such serologically "incomplete" antibodies are believed to be fully functional bivalent IgG molecules, but they are unable to bridge two cells and hence do not produce positive agglutination.

SUMMARY OF THE INVENTION

Accordingly, it is an object of the present invention to provide a hemagglutination reagent having an improved capacity to agglutinate erythrocytes.

It is a further object of the present invention to provide an agglutination method, useful for assaying erythrocyte antigens, which is rapid and sensitive.

It is yet a further object that human erythrocyte surface antigens, which are not normally capable of producing visible hemagglutination, may be agglutinated and the clumps subject to detection.

In one aspect of the present invention, an agglutination method useful for assaying cell surface antigens comprises providing a quantity of liposome-protein conjugates where the protein thereof supplies an antigen binding capacity for at least a majority of the liposome-protein conjugates, contacting the liposome-protein conjugates with substantially unagglutinated cells to form a mixture, and examining the mixture for cell agglutination. The liposome-protein conjugates have at least about 40 micrograms of protein per micromole of lipid.

In another aspect of the present invention, a reagent, useful for hemagglutination, comprises liposome-protein conjugates having an antibody covalently bound to the liposomes and an antigen binding capacity for erythrocytes bearing a surface antigen for which the antibody is specific. The reagent has a hemagglutinating activity which is improved with respect to the hemagglutination activity of the original antibody from which the liposome-protein conjugates are derived.

The liposome-protein conjugates and method of the present invention provide considerably improved sensitivity for agglutination assays. For example, agglutination of erythrocytes by use of the liposome-protein conjugates can occur in seconds with large, clearly visible agglutinated clumps of cells. By contrast, agglutination assays using the original, soluble antibody typically require minutes to produce agglutination visible to the naked eye, and the clumps of cells are much smaller. Thus, the ability of liposome-protein conjugates in accordance with the present invention to produce larger, more visible clots suggests the possibility of simple, visual spot tests which need not require special optical equipment for observation, and for use in a variety of diagnostic applications.

DETAILED DESCRIPTION OF THE PREFERRED EMBODIMENTS

Broadly, one aspect of the present invention is a diagnostic method wherein liposome-ligand conjugates are contacted with ligand-binding molecules to form a mixture, and the mixture is examined for combinations, or interactions, between the liposome-ligand conjugates and the ligand-binding molecules. The ligand-binding molecules are carried by at least one surface, more preferably carried by a plurality of surfaces defined by discrete particles, and most preferably carried by cell surfaces. The ligand of the liposome-ligand species is in an amount of at least about 40 micrograms per micromole of lipid, and preferably is a protein having an antigen binding capacity. For example, when the protein is an antibody and the ligand-binding molecules are antigens carried by cell surfaces, then the mixture examination following the contacting step typically includes determining cell agglutination mediated by combinations between the coupled antibody and immunological partners, or specific antigens, carried on the cells. Where the ligand is protein, the conjugates will hereinafter sometimes be referred to as liposome-protein conjugates.

The at least one surface carrying the ligand-binding molecules may be a natural multivalent antigen or may also be formed by inanimate, synthetic materials. For example, among suitable non-cellular materials are polyacrylamide beads about 5-10 microns in diameter having immobilized, or covalently bound, immunoglobulin on the bead surfaces, which are commercially available from Bio-Rad Laboratories under the trademark "Immunobead", and polystyrene spheres about 1 micron in diameter, which may be coupled along their surfaces with immunoglobulin such as IgG, commercially available from Covalent Technology Corp. under the trademark "Covaspheres".

As used herein, ligand and ligand-binding molecules mean moieties which can interact specifically but non-covalently with each other. One type of such moiety pairings is an antigen-antibody interaction, another is a hormone-receptor interaction, and yet another is a carbohydrate-lectin interaction.

Liposome-protein conjugates useful in accordance with the present invention may be prepared in various ways. For example, one suitable preparation is via activated liposome precursors where the precursor liposomes, before being covalently bound, are activated by means of an oxidizing reagent. A modification of this preparation is wherein the lipid, such as gangliosides, is first oxidized and then formed into the precursor liposomes. Another suitable preparation is via disulfide bonds, as described by Martin et al, supra.

In any event, it is necessary that the protein be then covalently bound to the liposomes precursors in an amount of at least about 40 micrograms per micromole of lipid. A suitable preparation and properties of liposome-protein conjugates will now be more fully described.

Preparation of Liposome-Protein Conjugates Via Activated Liposome Precursors Activated liposomes may be prepared from starting vesicles which are generally characterized either as unilamellar vesicles or multilamellar vesicles. Either liposomal structure is suitable. A particularly preferred preparation is by the reverse-phase evaporation vesicle (REV) method, which is disclosed by U.S. Pat. No. 4,235,871, as is described in *Proc. Natl. Acad. Sci. U.S.A.*, Volume 75, No. 9, pp. 4194–4198 (1978), entitled "Procedure For Preparation of Liposomes With Large Internal Aqueous Space And High Capture By Reverse-Phase Evaporation", Szoka, Jr. and Papahadjopoulos, which disclosures are incorporated herein by reference.

As is known to the art, a wide variety of materials may be encapsulated, if desired, by the precursor liposomes. For example, the precursor liposomes can encapsulate cytotoxic drugs, can encapsulate nucleic acids, and can encapsulate various proteins.

In any event, the precursor liposomes suitable for the present invention may be formed from either phosphatidylglycerol (hereinafter also referred to as "PG"), which has an oxidisable group at the polar head region, as the sole lipid, or may be formed from a mixture of two or more different lipids.

When formed from two or more different lipids, at least one of the lipids contains oxidisable groups, such as vicinal amino or vicinal hydroxyl groups, along the polar head region of the lipid molecule. For example, in the instance of vicinal amino groups, a glycolipid having galactosamine or glucosamine residue is a suitable oxidisable lipid. More usually, at least one of the lipids will have vicinal hydroxyl groups at the polar head region. Particularly preferred as one of the lipids (that is, the oxidisable lipid) in a lipid mixture are the glycolipids such as lactosyl ceramide, galactocerebroside, gangliosides, and trihexosyl ceramide, and the phospholipids, such as phosphatidylclycerol and phosphatidylinositol.

The amount of such lipids having oxidisable groups (generally herein referred to as "oxidisable lipids") may vary with respect to the total lipids forming the precursor liposomes; however, it is preferred that the mole percent of oxidisable lipids be in an amount of at least about 10 mole percent with respect to a total of the mixture of lipids.

Particularly preferred amounts of oxidisable lipids with respect to the total lipids are illustrated by Table I, below.

TABLE I

| Oxidisable Lipid | Mole of Oxidisable Lipid To Total Lipid Mixture |
|---|---|
| Lactosylceramide | About 10 |
| Trihexosylceramide | About 10 |
| Galactocerebroside | About 20 |
| Phosphatidylglycerol | About 33–40 |
| Phosphatidylinositol | About 20 |
| Gangliosides | About 10 |

The structures of the preferred oxidisable lipids are well known; however, for clarity FIG. 1, below, illustrates PG as representative of the general structures of the oxidisable lipids having the polar head regions and the region of non-polar tails.

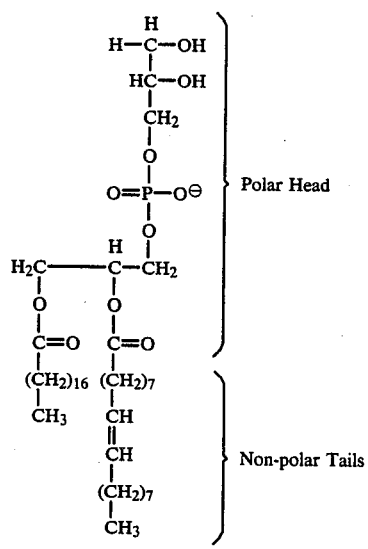

Figure I: PG

FIG. 1 is generally representative of all of the lipids which may be mixed to form the precursor liposomes in defining the polar head region and the non-polar tails. The FIG. 1 structure is more particularly generally representative of the oxidisable lipids which have vicinal hydroxyl groups at the polar head region thereof.

When a mixture of lipids, including the oxidisable lipid, is utilized to form the precursor liposomes, then the remaining lipid or lipids may include any of the amphiphilic substances known to produce liposomes. A particularly preferred lipid for combination with the oxidisable lipids is phosphatidylcholine (hereinafter also referred to as "PC"), sphingomyelin or mixtures thereof.

As is known, the above discussed mixtures of lipid molecules form precursor liposomes with the lipid molecules being arranged in either one bimolecular layer (unilamellar) or a plurality of bimolecular layers (multilamellar). In any event, the most outward bimolecular layer forms an outer surface for the liposome. In an aqueous solution, the polar head regions of the lipid molecules are exposed, or extend into, the aqueous system in a generally radially outward orientation with respect to the outer surface. The non-polar tails extend radially inwardly with respect to the outer surface and form a substantially continuous hydrocarbon phase of the bimolecular layer. This substantially continuous hydrocarbon phase is relatively impermeable, and acts to encapsulate the materials inside the precursor liposomes.

Nevertheless, some mixtures of lipids forming the precursor liposomes may tend to be permeable to small molecules, and cholesterol is a desirable addition to some of these lipid mixture for reducing the permeability of the precursor liposomes. The cholesterol tends to orientate within the bimolecular layer. Other components may be utilized in place of cholesterol to reduce the liposome permeability. For example, a phosphatidylcholine having the fatty acid saturated aliphatic chain, or non-polar tails, of a length of 18 (rather than the usual unsaturated 16 to 18 carbon chain obtainable from egg yolks) may be utilized. However, when sphingomyelin is mixed with the oxidisable lipid, the precursor liposomes thereof are inherently quite impermeable to small molecules.

A solution of precursor liposomes may thus be provided as has been described above. This solution is preferably a polar solution, such as an aqueous solution, but may also be a non-polar solution. The precursor liposomes are contacted with a sufficient amount of a relatively mild oxidizing reagent to produce activated liposomes. Where the lipids to be used for liposomes are in a non-polar solution, the oxidizing reagent may be lead tetraacetate. In the preferred polar solution, the oxidizing reagent of the contacting step is a periodate reagent, usually sodium periodate, which cleaves the vicinal amino or hydroxyl groups at the polar head regions of the oxidisable lipids.

Where the solution is polar and the oxidizing agent is a periodate reagent, the pH and osmolarity of the liposome solution and an added amount of periodate reagent should be substantially the same. The pH is typically about 6.0 to about 8.5. The oxidizing reagent produces activated liposomes by oxidizing the oxidisable groups, such as the vicinal hydroxyl or amino groups of the oxidisable lipid, to yield aldehyde moieties at the polar head regions of the oxidisable lipids. A sufficient quantity of periodate reagent will usually be a molar ratio with respect to the total of lipid molecules of from about 1.5:1 to about 6:1. The oxidation reaction of the contacting step is typically left to proceed for about one-half hour at room temperature, although the reaction may be permitted to proceed for up to about one hour on ice. The periodate reagent is then preferably removed by gel filtration through a column of dextran polymeric beads having an exclusion limit of about 75.000 daltons.

Reaction Schemes I, II and III diagrammatically illustrate the activation of precursor liposomes, with the oxidisable lipids being phosphatidylglycerol, phosphatidylinositol and lactosylceramide respectively.

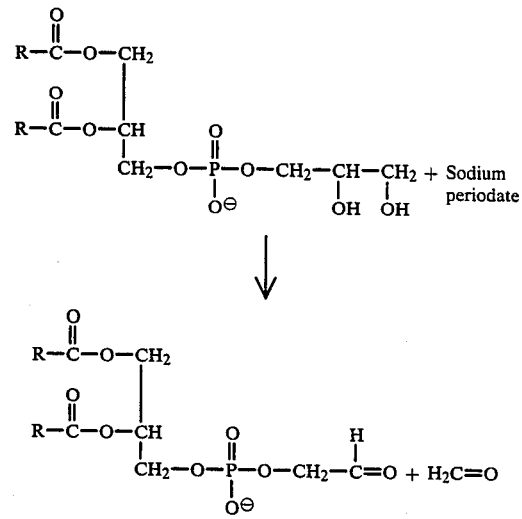

Reaction Scheme I

Reaction Scheme II

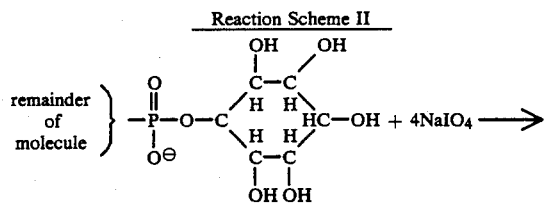

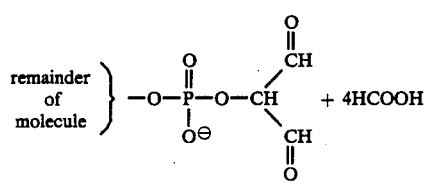

Reaction Scheme III

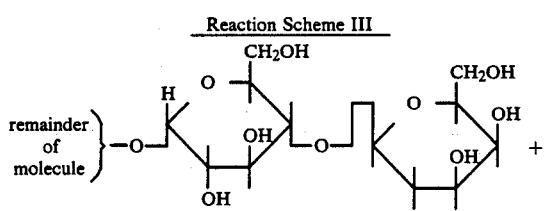

Sodium periodate ⟶ HCOOH +

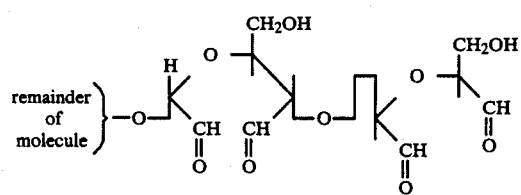

Substantially all of the material which is interior the outer surfaces of the activated liposomes remains encapsulated during the above-described oxidation with periodate reagent. As illustrated by Reaction Schemes I–III, the aldehyde moieties which are formed by the oxidation, or modification, of the oxidisable lipids at the polar head regions thereof define covalent binding sites for the protein to be bound, or coupled.

A wide variety of proteins may be attached, or coupled, to the activated liposomes. The mechanism of coupling is believed to occur between the primary or secondary amino group along the protein and the aldehyde moiety of the activated liposomes so as to form a Schiff-base, for example, with the primary amino group of a lysyl moiety. Such a mechanism is diagrammatically represented by Reaction Scheme IV, which for simplicity illustrates only the terminal galactose (after modification) of lactosylceramide.

Reaction Scheme IV

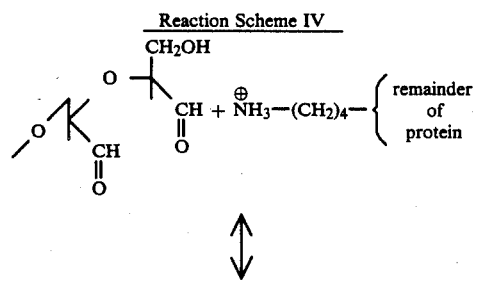

⇕

-continued
Reaction Scheme IV

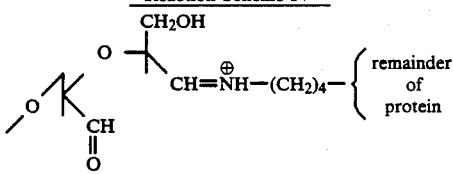

The coupling is driven to completion by a mild reducing agent, preferably sodium cyanoborohydride, so that a stable, covalent bond is formed between the protein and the activated liposome. For example, addition of a sufficient amount of sodium cyanoborohydride drives the Schiff-base of reaction Scheme IV, above, to completion, as is generally illustrated by Reaction Scheme V, below.

Reaction Scheme V

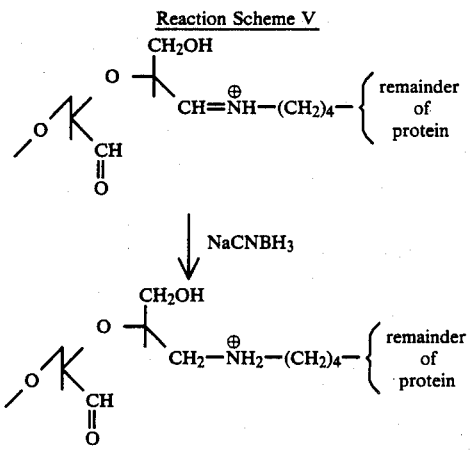

Reaction Schemes IV and V, above, diagrammatically illustrate coupling of a protein with lactosylceramide, where the lactosylceramide has been modified by oxidation to include aldehyde moieties. Use of the other oxidisable lipids proceeds by an analogous manner. In the instance of modified lactosylceramide, the secondary amine moiety which is covalently binding the protein to the activated liposome may further proceed, in the presence of sodium cyanoborohydride, into an even more stable, tertiary amine form.

Although sodium cyanoborohydride is the preferred reducing agent for coupling proteins to the activated liposomes, other reducing agents may be utilized, depending upon the particular circumstances. For example, borohydride may be utilized; however, the coupling reaction would usually then be conducted at a relatively alkaline pH, which may tend to denature the protein being coupled.

Suitable proteins for adequate coupling will have at least one primary or secondary amino group, and preferably a plurality of primary or secondary groups. Proteins having at least about 20 lysyl moieties per molecule are more preferred. IgG, with about 60 lysyl moieties, has been found to be particularly well coupled; another preferred antibody for coupling with the activated liposome is F[ab']$_2$.

Four aqueous solutions of liposome, each containing from about 10 to about 40 micromoles of lipid per milliliter, were activated as previously described. The precursor liposomes had been prepared by the REV procedure and had been extruded through a polycarbonate filter to yield liposomes having a diameter of about 0.2 micron. The solutions were buffered at a pH of from about 6.0 to about 8.5. A fifth liposome solution, wherein the oxidisable lipid was not oxidized, was prepared as a control. These four activated liposome solutions in accordance with the present invention and the fifth control solution were as illustrated by Table II.

TABLE II

| Solution No. | Lipid Composition Molar Ratio | Total Lipid (micromole) | Vol. (ml.) |
|---|---|---|---|
| 1 | PC/Lactosylceramide, 10:1 | 9.21 | 2.8 |
| 2 | PC/Trihexosylceramide, 10:1 | 16.44 | 4.5 |
| 3 | PC/PG, 1:1 | 9.5 | 3.1 |
| 4 | Galactocerebroside/ PC/Cholesterol, 2:4:5 | 15 | 0.6 |
| 5* | PC/Lactosylceramide, 10:1 | 7.11 | 2.8 |

*Control solution, liposomes not activated

The five solutions as in Table II were treated as follows. 5 to 10 milligrams of IgG in the same buffer as the liposome solutions were added to the respective liposome solutions (the activated liposomes were suspended in the solutions with substantially no clumping). Sufficient sodium cyanoborohydride was added to give a concentration of about 20 millimolar, and the solutions were left for about 2 to about 3 hours at room temperature. The liposomes having covalently bound IgG thereon were then purified by conventional methods, such as column gel filtration or centrifugation. The amount of coupling is illustrated by Table III, below (the number of molecules per vesicle was estimated on the assumption that the vesicles were 0.2 micron in diameter, with about $1.8 \times 10^{12}$ vesicles/micromole lipid).

TABLE III

| Liposome Solution | IgG (mg) added | Protein:Lipid Ratio (μg/mole) | (μg/mg lipid) | Molecules IgG/vesicle |
|---|---|---|---|---|
| 1 | 20 | 112 | 147 | 251 |
| 2 | 14 | 57 | 75 | 128 |
| 3 | 14 | 47 | 62 | 106 |
| 4 | 10 | 96 | 126 | 216 |
| 5* | 20 | 11 | 14 | 25 |

*Control solution, liposomes not activated.

Binding of Protein to Liposomes

IgG coupling to activated liposomes has typically resulted in the binding of from about 50 to about 200 micrograms of IgG per micromole of lipid. Substantially no coupling is observed in control liposomes. Nonspecific binding of proteins to activated liposomes was below the limits of the protein assay utilized in determining coupling.

The proteins which may be covalently bound, or coupled, to the activated liposomes retain a significant amount of biological activity. This is illustrated by use of immunopurified rabbit and antifluorescein antibody, as follows.

Antifluorescein IgG binds specifically to fluorescein isothiocyanate and carboxyfluorescein. Upon binding to the antibody, the fluorescence of the fluorescein is abolished, and this was used to measure the binding activity of the antibody. Successive additions of antibody to a solution of carboxyfluorescein reduced the fluorescence due to quenching of the fluorophore upon binding to the antibody. The antigen binding capacity of liposome-bound antibody was compared by correlating the percentage reduction in fluorescence for a variety of specified protein concentrations in linear ranges where quenching was proportional to the protein concentration as illustrated by Table IV, below (wherein the original antibody, or control, linear range was from about 78/1 to about 30/4; unbound antibody was from about 85/1 to about 40/5; and coupled antibody-activated liposomes was linear over the entire range illustrated).

TABLE IV

| Fluorescent Intensity/Antibody conc. $\times 10^8$ (μmole/ml) | | |
|---|---|---|
| Original Antibody (Control) | Unbound Antibody | Coupled Antibody-Activated Liposome |
| 78/1 | 85/1 | 95/1 |
| 60/2 | 75/2 | 90/2 |
| 40/3 | 62/3 | 85/3 |
| 30/4 | 50/4 | 78/4 |
| 18/5 | 40/5 | 70/5 |
| 12/6 | 35/6 | 65/6 |
| 8/7 | 30/7 | 60/7 |
| 8/8 | 20/8 | 58/8 |
|  | 15/9 | 50/9 |

As illustrated by Table IV, above, the fluorescent quenching of carboxylfluorescein by the original antibody preparation (control) and the antibody that was recovered from the coupling process may be compared to antibody bound to the activated liposomes. If the activity of the original, control preparation is set at 100%, then the activity of the activated liposome bound antibody is about 33%, and of the recovered antibody is about 70%. Antigen binding capacity is, therefore, only partially inhibited by the inventive coupling process, and the coupled protein displays, or retains, a significant amount of antigen binding capacity.

Hemagglutination

Liposome-protein conjugates in accordance with the present invention have the ability to agglutinate erythrocytes. Activated liposomes, prepared as described above, were conjugated with antigen-antibody, and incubated with erythrocytes conjugated with fluorescein-isothiocyanate. This resulted in the agglutination of the erythrocytes and the hemagglutinating titre (expressed as the minimum concentration observed to cause agglutination) was improved by a factor of about 1.5 with respect to the original, soluble antibody from which the liposome-protein conjugates were derivjed. Lower values of the hemagglutinating titre indicate more effective agglutination capacity. This is illustrated by Table V, below.

TABLE V

| Hemagglutination of FITC-Human Erythrocytes by Rabbit Antifluorescein IgG | |
|---|---|
| Preparation | Titre (microgram/ml) |
| Liposomes Bound Antibody (500 molecules/vesicle) | 1.22 |
| Untreated Antibody | 1.92 |

The improved ability of liposome-protein conjugates in accordance with the present invention to agglutinate erythrocytes is also demonstrated in another preparation of liposome-protein conjugates via the activated liposome precursors, as follows.

10 mg of F[ab']$_2$ was added to 10 μmole of vesicle lipid (after oxidation and desalting) in 1 ml of borateasline (pH 8.4), and then added 10 μl of 1M sodium cyanoborohydride. After 18 hours at room temperature, the vesicles were separated from unbound protein by flotation on discontinuous dextran gradients (0 to 20 percent, weight to volume). For quantitation of binding to cells the vesicles contained $^3$H-labeled dipalmitoylphosphatidylcholine (DPPC; 10 $\mu$Ci/$\mu$mole) and $^{14}$C-labeled sucrose (1 $\mu$Ci/$\mu$mole). "Targeted" vesicles were those having coupled rabbit F[ab']$_2$ to human erythrocytes, whereas "control" vesicles were coupled to F[ab']$_2$ prepared from rabbit gamma globulin by pepsin digestion and absorption to a *Staphylococcus aureus* suspension.

The targeted vesicles and the control vesicles were then separately incubated with $10^6$ to $10^8$ human erythrocytes in 0.2 ml of phosphate-buffered saline (PBS) at pH 7.4 for 1 hour at 37° C. Cells were washed to remove unbound vesicles and were either taken up directly in 10 ml of Triton-toluene scintillant and counted for [$^3$H]DPPC ($10^6$ to $10^7$ cells) or extracted after washing $10^8$ cells; the chloroform phase was evaporated and counted for [$^3$H]DPPC content, and the aqueous phase was incubated overnight at 60° C. to remove methanol and counted for [$^{14}$C]sucrose content.

When vesicles (with from about 1 to 500 nmoles of lipid) were incubated with $10^8$ cells there was a marked difference between targeted and control binding, with 80% of the vesicles binding at about 20 to 500 $\mu$mole of lipid. Control binding with vesicles conjugated to nonspecific F[ab']$_2$ was very low (<1 percent) and did not appreciably increase between 100 and 500 nmole of lipid). Both the vesicle lipids and the encapsulated sucrose bound to the cells in nearly identical proportions, indicating that cell binding caused no loss of vesicle contents and that the antibody-conjugated liposome preparation was reasonably homogeneous with respect to lipid, encapsulating aqueous marker, and antibody. When vesicles were incubated with $10^7$ erythrocytes there was a marked difference in binding between the targeted and non-targeted samples. Although a small fraction of the total available vesicles became bound, the number of vescles that bound to each cell was increased. Vesicles incubated with $10^6$ cells also exhibited binding specificity (not shown), with 6 nmole of specific antibody-bearing vesicles and 2 nmole of non-specific vesicles being bound when 100 nmole of lipid was incubated with the cells. The addition of serum (25 percent fetal calf) during incubation had no substantial effect on the binding.

The vesicle preparations contained 143 molecues per vesicle, assuming F[ab']$_2$ has a molecular weight of 90,000 and that the vesicle preparations contained $1.8 \times 10^{12}$ vesicles per micromole (for unilamellar vesicles of 0.2 $\mu$m diameter). Antibodies not purified immunologically, such as those used here, may contain only 1 to 5 percent of molecules that are specifically reactive to the cell antigens. The preparation therefore probably contained approximately one to five specific molecules per vesicle, so that most vesicles were specific for the target cells. The use of nonimmunopurified antibodies with coupling method that bind only a few antibody molecules per vesicle would result in many vesicles having no specificity for the target.

The association of 400 nmole of lipid with $10^8$ human erythrocytes constitutes a lipid mass three times greater than the lipid content of the cell membranes. If one assumes that the vesicles are 0.2 $\mu$m in diameter and are unilamellar, the number of vesicles bound per cell is 8000 and their encapsulated volume is 0.33 of the cell volume. Thus, about 80% of the targeted vesicles associated with the human erythrocytes.

The hemagglutinating titre of the F[ab']$_2$ bound to vesicles was measured and compared to the original antibody preparation. The nonspecific soluble F[ab']$_2$ and the control vesicles derived from it produced no hemagglutination at concentrations up to 1 mg of F[ab']$_2$ per milliliter. The soluble antibody to human erythrocyte F[ab']$_2$ had a hemagglutination tire of 4 $\mu$g/ml, and the titre of the liposome-protein conjugates derived from the original, soluble antibody was 1.5 $\mu$g/ml, for an improvement factor of about 2.7.

The extent of improvement, or enhancement, of hemagglutinating activity for suitable liposome-protein conjugates is greater than appears from the data, for example in Table V, since during conjugation some of the bound antibody is partially inactivated. In a further experiment, performed with antifluorescein conjugated liposomes prepared via the activated method, a variety of antibody preparations were obtained by mixing the immunopurified antifluorescein with normal rabbit IgG to vary the extent of antifluorescein substitution. The activity of the antifluorescein was calculated by fluorescence quenching, as previously described and illustrated by Table IV, and this value was used to calculate the number of active antibody molecules per liposome of the liposome-antibody conjugates and the corrected minimum hemagglutinating concentration. The liposome-protein conjugates were contacted with unagglutinated erythrocytes which had been coated with fluorescein. (The uncorrected minimum hemagglutinating concentration (MHC) is calculated from the total protein concentration.) The data is illustrated by Table VI, below.

TABLE VI

| Active antibody molecules/liposome | MHC ($\mu$g/ml) | corrected MHC ($\mu$g/ml) | Improvement factor |
|---|---|---|---|
| 67 | 5.10 | 1.63 | 2.3 |
| 100 | 1.60 | 0.70 | 5.6 |
| 186 | 0.57 | 0.31 | 12.6 |
| soluble antibody | 3.90 | 3.90 | — |

The improvement factor, illustrated by Table VI, above, compares the corrected MHC of lipsome-protein conjugates to the MHC of the original, soluble antibody from which the liposome-protein conjugates were derived. As may be seen, the improvement factor varied from about 2.3 to about 12.6, depending upon the number of active antibody molecules which were covalently bound per liposome.

In another preparation of liposome-protein conjugates the liposome-protein conjugates had 50 $\mu$g of antihuman erythrocyte Fab' fragments per $\mu$mole liposomal phospholipid (about 500 antihuman Fab' fragments per liposome). The precursor liposomes were formed from PC:cholesterol:PDP-PE and conjugated to Fab' by the procedure of Martin and Papahadjopoulos, *J. Biol. Chem.*, (1981-In Press). The minimum hemagglutinating concentration (MHC) for soluble antibody was 5.2 $\mu$g/ml, whereas the MHC for liposome-protein conjugates was 0.17 $\mu$g/ml. That is, the agglutination improvement factor was about 30.

Binding Inhibition

Another batch of liposome-protein conjugates via activated liposome precursors was prepared and tested with soluble antibody for binding inhibition as follows.

The precursor liposomes were prepared from a mixture of phosphatidylcholine:cholesterol:oxidized ganglioside (5:5:1) which contained trace amounts of $^3$H dipalmioylphosphatidylcholine to give 2000 counts per minute (cpm) per nanomole lipid. These vesicles were then conjugated to monoclonal mouse anti H2K$^k$ antibody by reductive amination with sodium cyanoborohydride. The resultant liposome-protein conjugates had an antibody:lipid ratio of 60 μmole.

Meanwhile, 5×10$^6$ L929 fibroblasts in confluent monolayers in 6 cm petri dishes were incubated for 30 minutes at 37° C. with 0.2 ml phosphate buffered solution (PBS) containing 50% serum and 20 nmole lipid to which was conjugated 1.2 μg antibody. The incubation mixture also contained variable amounts of soluble antibody, as indicated in Table VII, below. After incubation, the cells were washed four times with phosphate buffered saline, trypsinized to remove them from the monolayer and taken up in scintillant for counting.

In a similar manner, 2×10$^6$ R1.1 T-lymphoma cells were suspended in 0.2 ml PBS containing 50% serum, 20 nmole lipid conjugated to 1 μg antibody and various amounts of soluble antibody as indicated in Table VII, below. After 30 minutes they were washed four times by centrifugation and resuspension of the cells in 5 ml portions of PBS. The cells were finally resuspended in 0.5 ml and taken up in scintillant.

The antibody-anti H2K$^k$ reaction which occurred between the liposome-conjugates and the cells (and, to a lesser extent between the soluble antibody and the cells) illustrates a reaction with the H2K of certain mouse strains. This protein is a membrane antigen present at high levels in most mouse tissues. The L929 fibroblast and the R1.1 T-lymphoma are cultured cell lines derived from mice which express the H2K$^k$ antigen.

TABLE VII
INHIBITION OF TARGETED LIPOSOME BINDING BY SOLUBLE ANTIBODY

| Soluble Antibody | Percent Control Binding | |
|---|---|---|
| Per Sample (μg) | L929 | R1.1 |
| 0.1 | 100% | 100% |
| 0.3 | 86% | 97% |
| 1 | 97% | 81% |
| 3 | 100% | 62% |
| 10 | 95% | 44% |
| 30 | 66% | 31% |

For example, as illustrated by Table VII above, a ratio of soluble to liposome-bound antibody of at least 10:1 was required to achieve about 50% binding inhibition with the R1.1 T-lymphoma cells. These data demonstrate that liposome-protein conjugates in accordance with the present invention bind with greater functional affinity to their immunological partners than does soluble antibody. It is believed this, and the improved agglutination property, is due to a multivalent character of the liposome-protein conjugates, e.g. that each vesicle contains many antigen binding sites. By contrast, for example, native IgG is only bivalent.

A wide variety of proteins particularly antibodies, may be covalently bound to liposomes and used in accordance with the present invention. Table VIII, below, illustrates a number of liposome-protein conjugates suitable for immunodiagnostic applications, and particularly for cell agglutinations mediated by combinations with the appropriate antigenic partner.

TABLE VIII

| liposome-protein conjugate composition # | bound antibody | antibody to lipid ratio (μg/μmole) |
|---|---|---|
| 1 | Normal bovine IgG | 100–300 |
| 2 | Normal rabbit IgG | 60–300 |
| 3 | Normal rabbit F[ab']$_2$ | 70 |
| 4 | Rab. antiHRBC F[ab']$_2$ | 60 |
| 5 | Mouse IgG | 98 |
| 6 | Rabbit anti CVI | 107 |
| 7 | Normal rabbit IgG | 275 |
| 8 | anti sheep RBC (2a)* | 153 |
| 9 | anti H2K$^k$ (2a)* | 72 |
| 10 | anti Thy 1.1 (1)* | 50 |
| 11 | anti sheep RBC (2a)* | 121 |
| 12 | anti H2K$^k$ (2a)* | 70 |
| 13 | Normal human IgG | 235 |
| 14 | anti H2K$^k$ (2)* | 52 |
| 15 | Mouse IgG (All)* | 128 |
| 16 | anti glycophorin (1)* | 240 |
| 17 | anti sheep RBC (2a)* | 2000 |

(*wherein the symbol within the parentheses gives the IgG subclass of the antibody)

Composition numbers 1–10, above, were prepared from precursor liposomes by the activated liposome method (e.g. glycosphingolipids were oxidized with periodate and antibody was covalently bound by reductive amination with sodium cyanoborohydride). The lipid of compositions 1 and 2 were lactosylceramide, phosphatidylglycerol, phosphatidylcholine and cholesterol in a ratio of 10:3:45:45. The lipid of compositions 3–10 consisted of phosphatidylcholine, cholesterol and ganglioside in a ratio of 5:5:1. The antibody of compositions 8–10 was monoclonal (mouse).

Compositions 11 and 12 were prepared from precursor liposomes by a preoxidation modification of the activated liposomes method (e.g. gangliosides were preoxidized, the precursor liposomes were formed therefrom, and the antibody then conjugated as in the activated liposome method). More particularly, gangliosides, usually a mixture from bovine brain, are suspended in 20 mM sodium-in-periodate at pH 5.5. After 30 minutes at room temperature in the dark, ethylene glycol is added to a final conc of 100 mM and the solution is left 30 minutes. Oxidized gangliosides are separated from the reaction products by gel chromatography. The ganglioside fractions are pooled, mixed with methanol and evaporated to dryness under a stream of nitrogen. The residue is taken up in chloroform:methanol (1:1) and stored under argon at −40° C. before protein conjugation. Lipid content was as described for compositions 3–10, above. The antibody was monoclonal (mouse).

Compositions 13–17 were prepared as follows. N-[4-(p-maleimidophenyl)butyryl]phosphatidylethanolamine (MPB-PE) was synthesized by the procedure of Martin and Papahadjopoulos, *J. Biol. Chem.* (1981—In Press). Liposomes are then prepared by the method of Szoka and Papahadjopoulos, supra, from 10:10:1 phosphatidylcholine:cholesterol:MPB-PE in a buffer at pH 6.0–6.7. A suitable buffer is 0.05M morpholino-ethanesulfonic acid, 0.096M NaCl, pH 6.4. It is essential to prepare the vesicle below pH 7.0 to ensure the maximal stability of the maleimide function. The antibody is pyrdiylthiolated and reduced by the method of Carlsson et al. *Biochem. J.*, 173, pp. 723–737 (1978). Reaction of protein with 10 mole of N-Succinimidyl 3-(2-Pyridyldithio) Proprionate (SPDP) per mole of protein results in the substitution of 3–5 mole of pyridyldithiol groups per mole protein. After reduction with dithiothreitol, the protein is separated from the reducing agent on a polyacrylamide column (50 to 100 mesh) equilibrated in argon-purged (de-oxygenated) buffer, pH 6.0–6.5. The protein fractions are pooled and concentrated to a suitable volume under argon in an amicon type concentrator. Commonly, the protein is concentrated to around 3 mg/µl. Liposomes are then added to the protein solution with stirring to give 5 µmole lipid per ml. After reaction overnight, the vesicles are reacted with Aldrithiol 4 and separated on a metrizamide gradient and the protein and lipid are determined.

The protein, or antibody, was modified in compositions 13–17 by from about 1.8 to about 5.1 thiols per molecule.

Industrial Applicability

The enhanced agglutination activity of liposome-protein conjugates is useful for a variety of diagnostic applications, such as in inhibition assays and flocculation tests. Hemagglutin inhibition assays measure the extent to which a soluble antigen inhibits the capacity of its specific antibody to agglutinate antigen-sensitized erythrocytes. Liposome-protein conjugates can increase the sensitivity of hemagglutination inhibition assays. Since considerably less antibody is required for agglutination, a correspondingly less amount of soluble antigen will inhibit agglutination. That is, soluble antigen will compete with an erythrocyte surface antigen of the same antigenic specificity, and thus the presence of soluble antigen will reduce the amount of agglutination produced by liposome-protein conjugates specific for the antigen. One may thus determine the extent to which the soluble antigen inhibits cell agglutination mediated by antibody-antigen interaction. Among the human serum antigens which may be detected by the more sensitive liposome-protein conjugates are peptide hormones, such as thyroxin, C-reactive protein, hepatitis surface antigen, hCG, heterophile antibodies, rheumatoid antibodies, thyroxin binding protein ($T_3$) and digoxin.

In addition, liposome-protein conjugates may be used in flocculation tests. For example, where the liposome-protein conjugates have an antibody covalently bound to the liposomes, the antibody may be selected with an antigen binding capacity for a particle such as the Dane particle of hepatitis B virus, which would be more sensitively flocculated, or agglutinated, when contacted with the liposome-protein conjugates than when contacted with the original antibody from which the conjugates are derived.

The best mode contemplated for carrying out the present invention is use of liposome-protein conjugates in blood typing. The preferred size of liposomes for such use is from about 0.1 micron to about 5 micron, and more preferred from about 0.1 to about 0.5 micron.

The size is most preferably controlled by extrusion through straight pore polycarbonate filters, as is described in U.S. Pat. No. 4,263,428, issued Apr. 21, 1981. The extrusion permits the production of uniform vesicles in selected sizes between about 0.1 and about 0.5 micron.

The antibody preparation is covalently bound to the liposome so that the antibody is in an amount of at least about 40 microgram per micromole of lipid molecules, more preferably from about 40 to about 90 microgram per micromole of lipid. The antibody may be derived from a normal polyclonal antiserum, or from a monoclonal antibody. The liposome-protein conjugates are then separated from the soluble, unbound antibody by flotation in a discontinuous metrizamide gradient. The recovered liposome-protein conjugates may then be analyzed for protein and lipid content.

To establish the minimum quantity of the liposome-protein conjugates required for agglutination, serial two-fold dilutions of the liposome-protein conjugates are prepared in a hemagglutination plate (e.g. one half, one quarter, one eighth, one sixteenth, etc.). These dilutions are then mixed with an equal volume of a 2% erythrocyte suspension and left to stand for about 18 hours. The wells are then scored for agglutination, and the most dilute solution which gives agglutination is taken to be the minimum hemagglutination concentration.

Liposome-protein conjugates at a concentration known to give agglutination of antigen-positive cells are then mixed with erythrocytes whose expression of the antigen is to be determined. After incubation for a suitable period, the cells are scored for agglutination.

While the invention has been described in connection with specific embodiments thereof, it will be understood that it is capable of further modification, and this application is intended to cover any variations, uses or adaptations of the invention following in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A reagent, useful for hemagglutination assays, comprising:

conjugates comprising (a) liposomes and (b) antibody covalently bound to the liposomes, the liposomes having lipid molecules, the covalently bound antibody having an antigen binding capacity for erythrocytes, said erythrocytes bearing a surface antigen for which the covalently bound antibody is specific, to mediate hemagglutination via antigen-antibody interaction, the covalently bound antibody being in an amount of at least about 40 micrograms per micromole of lipid molecules, the conjugates having an enhanced hemagglutinating activity with respect to the hemagglutinating activity of antibody from which the conjugates are derived.

2. The reagent of claim 1 wherein:

the covalently bound antibody is derived from a polyclonal antiserum or is a monoclonal antibody, and the hemagglutinating activity is determinable as a minimum hemagglutinating concentration.

3. The reagent as in claim 1 wherein:

the enhanced hemagglutinating activity is at least about 1.5 times greater than the hemagglutinating activity of antibody from which the conjugates are derived.

4. The reagent as in claim 1 wherein:

the liposomes of the conjugates are from about 0.1 micron to about 5 micron in size.

5. The reagent as in claim 1 wherein:

the liposomes are a substantially uniform size between about 0.1 and about 0.5 microns.

6. The reagent as in claim 1 wherein:

the covalently bound antibody is IgG or a fragment thereof.

7. The reagent as in claim 6 wherein:

the IgG or fragment thereof is in an amount of from about 40 micrograms to about 90 micrograms per micromole of lipid molecule.

8. A reagent, useful for cell agglutination assays, comprising:

conjugates comprising (a) liposomes and (b) antibody covalently bound to the liposomes, the liposomes having lipid molecules, the covalently bound antibody having an antigen binding capacity for cells, said cells bearing a cell surface antigen for which the covalently bound antibody is specific, to mediate agglutination via antigen-antibody interaction, the covalently bound antibody being in an amount of at least about 40 micrograms per micromole of lipid molecules, the conjugates having an enhanced agglutinating activity with respect to the agglutinating activity of antibody from which the conjugates are derived.

9. The reagent of claim 8 wherein: the covalently bound antibody is derived from a polyclonal antiserum or is a monoclonal antibody.

10. The reagent as in claim 8 wherein: the liposomes of the conjugates are from about 0.1 micron to about 5 microns in size.

11. The reagent as in claim 8 wherein: the liposomes are a substantially uniform size between about 0.1 and about 0.5 microns.

12. The reagent as in claim 8 wherein: the covalently bound antibody is IgG or a fragment thereof.

13. The reagent as in claim 8 wherein the cells include fibroblasts or lymphocytes.

14. The reagent as in claim 8 wherein the covalently bound antibody includes IgG or Fab fragments which are attached to the lipid molecules of the liposomes through disulfide bonds.

* * * * *